(12) United States Patent
Pound et al.

(10) Patent No.: US 7,842,313 B2
(45) Date of Patent: Nov. 30, 2010

(54) SYSTEM AND METHOD FOR APPLYING MEDICATION TO A HOOF

(76) Inventors: Mark Pound, 2441 Flagstone Dr., Napa, CA (US) 94558; Kevin Graham, 2401 Citrine Way, Santa Rosa, CA (US) 95404

( * ) Notice: Subject to any disclaimer, the term of this patent is extended or adjusted under 35 U.S.C. 154(b) by 840 days.

(21) Appl. No.: 11/818,080

(22) Filed: Jun. 12, 2007

(65) Prior Publication Data

US 2008/0311222 A1    Dec. 18, 2008

(51) Int. Cl.
*A61K 33/34*    (2006.01)
*A61K 33/30*    (2006.01)
*A61K 47/10*    (2006.01)
*A61P 17/00*    (2006.01)
*A01L 15/00*    (2006.01)

(52) U.S. Cl. .................. 424/637; 424/630; 424/641; 424/642; 514/738; 168/2; 168/4

(58) Field of Classification Search ............... 424/630, 424/637, 641, 642; 514/738, 944, 946, 969
See application file for complete search history.

(56) References Cited

U.S. PATENT DOCUMENTS

| 5,780,064 | A  | * | 7/1998 | Meisters et al. | 424/616 |
| 6,412,566 | B1 | * | 7/2002 | Rovelli et al.  | 168/4   |
| 7,049,339 | B2 | * | 5/2006 | Thomson         | 514/494 |
| 7,537,063 | B2 | * | 5/2009 | La Croix        | 168/2   |

OTHER PUBLICATIONS

Downing, T.W. et al., "Case Study: use of copper sulfate and zinc sulfate in footbaths on Oregon dairies," The Pforessional Animal Scientist, vol. 26, (2010), pp. 332-334.*
MSDS Hooflex Thrush Remedy. [Retrieved on Sep. 28, 2010], Retrieved from the Internet:<URL: www.absorbine.com/dealer-pages/files/Absorbine_Hooflex_Thrush_Remedy_MSDS.pdf>.*

* cited by examiner

*Primary Examiner*—John Pak
(74) *Attorney, Agent, or Firm*—Dergosits & Noah LLP

(57) ABSTRACT

A gel that includes a fungicide or an anti-bacterial is contained within a single dosage packet that includes a tapered nozzle end and a body. The fungicide or anti-bacterial gel is applied to the hoof of a horse by opening the packet at the tapered nozzle end and squeezing the body. The gel is then spread over the frog and sole of the hoof with a portion of the packet. The gel is heated so that it spreads to recessed areas of the hoof that can contain the bacterial and fungus infections.

18 Claims, 3 Drawing Sheets

SYSTEM AND METHOD FOR APPLYING MEDICATION TO A HOOF

BACKGROUND

Common ailments of horses are diseases such as the growth of an infection around the hoof. The infection can be a bacteria or a fungus. The horse hoof is the structure surrounding the distal phalanx of each of the four limbs of Equus species, which is covered by complex soft tissue and keratinised structures. Since a single digit must bear the full proportion of the animal's weight that is borne by that limb, the hoof is of vital importance to the horse. The health and the strength of the hoof is crucial for horse soundness.

The hoof is made up by an outer part, the hoof capsule and an inner, living part, containing soft tissues and bone. The cornified material of the hoof capsule covers, protects and supports the foot bone and specialised soft tissues including: tendons, ligaments, fibro-fatty and/or fibrocartilaginous tissues and cartilage. The walls originate from the coronet band. Walls are longer in the anterior portion of the hoof, intermediate in length in the lateral portion and very short in posterior heel portion. Heels are separated by an elastic, resilient structure named the 'frog'.

The bottom of the hoof includes the wall's free margin that encircles most of the hoof and the triangular frog. Lateral to the frog are two grooves, deeper in their posterior portion, named 'collateral grooves'. At the heels, the posterior portion of the walls bend inwards sharply, following the external surface of collateral grooves. The lower surface of the hoof, from the outer walls and the inner frog and bars, is covered by an exfoliating keratinised material, called the 'sole'.

The walls cover and protect the sensitive internal hoof tissues and dissipating the contact energy and to provide grip on different terrains. The walls have a thickness of approximately 6 mm-12 mm. The walls are composed of distinct layers: the pigmented layer and the water line, which is also known as the white line, that merge in a single mass. Horseshoes are fixed to the walls by driving nails oblique to the walls. The nails enter the wall at the outside edge of the white line and they emerge at the wall's surface, approximately 15-20 mm from the base of the wall.

The frog is a triangular structure that extends forward across about two-thirds of the sole. Its thickness grows from the front to the back and, at the back, it merges with the heel periople. The frog has a rubbery consistency and functions as shock absorbers and improves the hoof's grip on hard, smooth ground. In the free-roaming horse, the frog hardens into a callous consistency with a near-smooth surface. In contrast, the frog of a stabled horse can degrade with bacterial and fungal activity into an irregular, soft, slashed surface.

There are various diseases that can infect a hoof. Thrush is a fungal disease which damages the frog and leaving open sores which eventually create significant pain and tenderness to the animal. The thrush may result in crippling of the horse if the condition is not treated. The frog and sole of the hoof can also be attacked by bacterial infections. Many treatments have been developed over the years. These treatments typically require anti-fungal and/or anti-bacterial chemicals and can be fairly difficult to apply to the hoof.

SUMMARY OF THE INVENTION

The inventive hoof fungus treatment method includes a treatment gel containing a mixture of copper sulfate, water and glycerin. These components can be mixed based upon a ratio of about 5-30% copper sulfate, 5-30% water and 40-80% glycerin. The mixture forms a gel having a viscosity of approximately 1-50 Cp (centipoises/milliPascal second).

A volume of gel corresponding to a single dosage is held in a small packet having a volume that can range from about 0.25 to 1.50 ounces. The packet can be a plastic material that is preferably clear and sealed. In an embodiment, the packet can include a body and a tapered section. By cutting or tearing the tapered section, the gel can be ejected from the packet. The user can place the cut section close to the frog and squeeze the packet to spread the gel over the frog and the sole.

The gel may have a translucent blue color from the copper sulfate so the user can see if there is gel remaining in the packet. In other embodiments, the gel can include dyes or other components that alter the appearance of the gel. The gel may have a light opaque color that is a strong contrast to the hoof and allows the user to see where the gel is spread across the hoof.

Because the gel has a high viscosity, it tends to stick to the hoof rather than running off like a low viscosity liquid. Once the required volume of the gel has been removed from the packet, the packet can have a rounded edge or a notched surface that is used to spread the gel across the frog and the sole. The empty packet can be discarded. Because the packet provides the required single dosage of the gel and a tool for spreading the gel on the hoof, the user can avoid direct contact with the gel. These features improve the convenience of the treatment method because there is no need for dealing with bulk materials and the cleaning after the medication has been applied is minimized.

The viscosity of the gel changes with temperature. After the gel is applied to the hoof, the body heat can cause the gel temperature to rise. Similarly, when a race horse runs, the hooves can heat up to 150° Fahrenheit due to the impact energy of the feet and shoe contact against the track. As the gel becomes less viscous it is able to flow into more recessed surfaces of the hoof which allows the improved treatment of the infection.

In other embodiments, the sole and frog are covered with a support pad made of an elastic material that can be held in place by the horseshoe. Any type or support pad can be used with the inventive method. In an embodiment, the pad can be made of an elastic material and may include an air bladder that supports the frog and a valve so the user can adjust the internal pressure of the bladder. The material can be placed over the frog and sole after the gel medication is applied as described to prolong the exposure of the infected areas to the medicated gel by preventing the removal due to contact with the track. Alternatively, the gel medication can be applied after the elastic material is attached to the hoof. In this embodiment, the tapered portion of the packet is opened and inserted in the space between the elastic material and the sole and frog. The gel medication is then injected into the space. The contact with the elastic material can help to spread the gel across the frog and sole.

DETAILED DESCRIPTION

Figure 1:
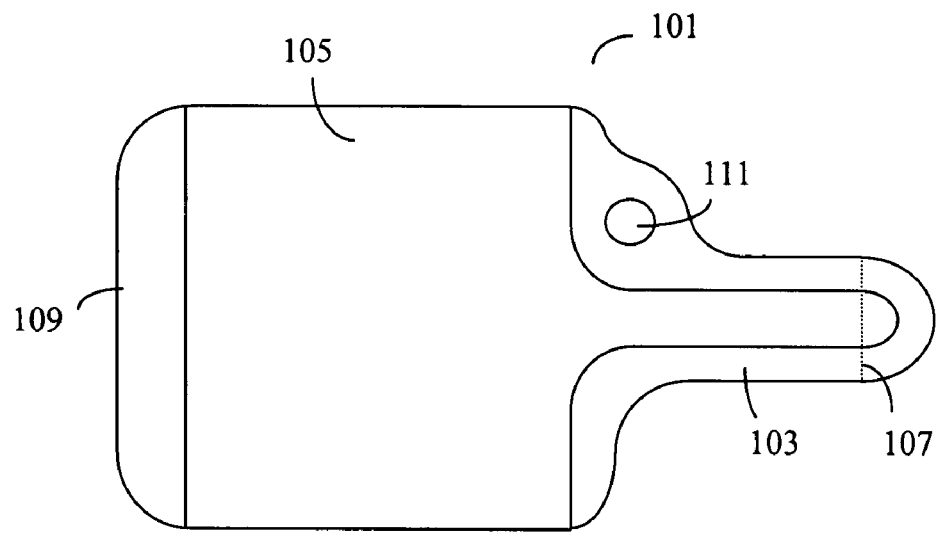
FIG. 1 illustrates a first embodiment of the packet containing the gel medication.

The present invention is an improved method for applying a medication to a horse hoof. The method can be used for various types of ailments including infections by bacteria and fungus. In an embodiment, the inventive method can be used for treating thrush and preventing the growth of fungus on the hoof of a horse. Horse hooves provide a good breeding ground for fungus because they are warm and damp. The horses can walk through mud, urine and fecal matter that can contain bacteria. In order to maintain the health of the horse, the hooves should be cleaned regularly by being picked out with a hoof pick any stones, mud and dirt. Keeping hooves clean and dry wherever possible helps prevent thrush fungus from growing. The hooves should be cleaned every time the horse is ridden, and if the horse is not ridden, it is still best practice to check and clean feet frequently. A weekly hoof check of horses is often sufficient during good weather. If thrush is detected, the inventive method can be used to cure the fungus infection before the frog and sole are damaged. A gel mixture containing copper sulfate is applied to the hoof to kill fungus on the frog and sole.

While copper sulfate is an effective medication that prevents the growth of fungus, it is mildly toxic to humans so physical contact should be minimized. Copper sulfate can be corrosive and is readily absorbed through the skin. Copper sulfate is also considered a skin sensitizer and can cause allergic reactions. Contact with copper sulfate can produce a burning pain and may result in itching or eczema. Ingestion can cause severe poisoning symptoms. In order to minimize direct contact, the user may wear protective clothing and gloves when applying the copper sulfate to the hoof.

The copper sulfate can be mixed with carrier ingredients to form a gel that is mostly liquid in composition but has the structural coherence of a solid. Since the gel has a higher viscosity than a liquid, it tends to adhere to other objects and remain in a coherent mass. The gel may not run out of the open packet unless the packet is compressed. This prevents the accidental spilling of the gel if the open packet is positioned on its side and reduces the chances of accidental contact with the copper sulfate.

Another added benefit of the gel is that a thick layer can be attached to the hoof. The gel tends to adhere to itself as a solid mass. Thus, a layer of the gel as applied to the hoof will adhere to the frog and sole surfaces. In contrast, a low viscosity liquid will separate if not confined within a container and does not have these adhesive properties. The high viscosity characteristics make it much easier to apply the gel than low viscosity liquids.

In an embodiment, the copper sulfate is mixed with glycerin and water. The percentages of each component are preferably within a range 5-25% copper sulfate, 10-25% water and 50-75% glycerin. In other embodiments, the concentrations can be 5-25% copper sulfate, 0-50% water and 25-85% glycerin. The copper sulfate dissolves in both water and glycerin which makes this combination of ingredients very uniform in a bulk mixture. Copper sulfate is blue and the gel that is formed from the mixture of copper sulfate, water and glycerin. The gel can therefore have a translucent blue color.

In other embodiments, additional liquid components can be added which can alter the appearance of the gel. For example, the gel can have an opaque light color which contrasts well with the hoof, such as white. This light color can be useful in determining how well the gel is spread across the hoof. If the hoof appears to be solid white, the user can easily determine that the gel has been spread across the entire hoof. Similarly, it allows the user to check the hoof to see if the gel has washed away and a new dosage should be applied.

Although the gel may be applied to the hoof at ambient temperature in a high viscosity state, the gel viscosity changes when warmed by the horses body heat. The viscosity of the gel varies with temperature and composition, primarily based upon the percentage of glycerin. A higher percentage of glycerin and/or a lower temperature will cause the gel to have a higher viscosity. Conversely, a lower percentage of glycerin and/or a higher temperature will have a lower viscosity of the gel. With reference to table 1 below, the approximate viscosities of the copper sulfate gel are listed with respect to percentage of glycerin and the temperature.

TABLE 1

| COMPOSITION | | | TEMPERATURE | | | | | | | |
|---|---|---|---|---|---|---|---|---|---|---|
| % Glycerin | % Water | % Copper Sulfate | 50° F. | 68° F. | 86° F. | 104° F. | 122° F. | 140° F. | 158° F. | 176° F. |
| 50 | 25 | 25 | 17.4 | 10.8 | 7.2 | 5.1 | 3.8 | 2.9 | 2.3 | 1.8 |
| 55 | 23 | 22 | 25.3 | 15.2 | 9.85 | 6.8 | 4.9 | 3.7 | 2.9 | 2.3 |
| 60 | 21 | 19 | 29.9 | 17.7 | 11.3 | 7.7 | 5.5 | 4.1 | 3.2 | 2.5 |
| 65 | 19 | 16 | 38.8 | 22.5 | 14.1 | 9.4 | 6.6 | 4.9 | 3.8 | 2.9 |
| 70 | 17 | 13 | 65.2 | 35.5 | 21.2 | 13.6 | 9.2 | 6.6 | 5.0 | 3.8 |
| 75 | 15 | 10 | 116 | 60.1 | 33.9 | 20.8 | 13.6 | 9.4 | 6.9 | 5.1 |

For a comparison of viscosities, table 2 includes a listing of viscosities of other more common gel type goods. Thus, the viscosity of the possible copper sulfate gel mixture can range from very runny honey to a thick ketchup.

TABLE 2

| Honey | Molasses | Chocolate Syrup | Ketchup |
|---|---|---|---|
| 2-10 | 5-10 | 10-25 | 50-100 |

As illustrated in Table, 1, the variation in viscosity of a gel is due to temperature. Thus, the gel tends to maintain its solid structure when it is applied to the hoof. The gel is then heated by the horse's body heat and become less viscose which causes the gel to flow into recessed areas of the hoof. The normal body temperature of a horse is 99° to 103° F. Thus, the hoof temperature may be only slightly lower than the body temperature. Another source of hoof heat is from the absorptive energy from the impact of the hoofs against a track surface. While running the hooves can get up to 150° F. As described above in Table 1, the increased temperature results in a lower viscosity.

A general concept is to apply the medical gel to the hoof in a high viscosity form that is easy to handle and then heat the gel so that it becomes lower in viscosity. The lower viscosity gel can have beneficial effects. For example, the lower viscosity may cause the gel to flow into recessed regions of the hoof which can be through capillary action. The lower viscosity gel then spreads over the recessed areas of the frog and hoof. These recessed areas can be particularly important because they tend to retain moisture and may be more susceptible to fungus growth. In some hot regions, the gel can be chilled so that it has a high viscosity when it is applied to the hoof. The gel is then heated and the gel viscosity decreases by the ambient temperature as well as the horse's body heat.

Although the heating of the hoofs has been described as being through the horse's body heat and running friction, it is also possible to heat the gel medication in many other ways. In an embodiment, the gel can be heated with a heat source such as a hair drier. In other embodiments, the horse can stand on a heated pad which can conduct through to the hooves to heat the gel.

The packaging of the gel can also be designed to reduce the risks of contact and provide a product that is safely and easily transported. With reference to FIG. 1, a single dose packet 101 is illustrated. The packet 101 can include a tapered nozzle section 103 and a body 105. The nozzle 103 can have a perforation 107 which allows the user to open the packet 101 by tearing or cutting the perforation 107. The packet 101 can also include an edge 109 which is used to spread the gel across the hoof. In this embodiment, the packet 101 also includes a hole 111 which allows the packet to be stored on a loop or rod. In an embodiment, a user can carry a loop of packets 101 so that when packet 101 is needed, the user can simply remove the packet 101 to treat the hoof.

Figure 2:
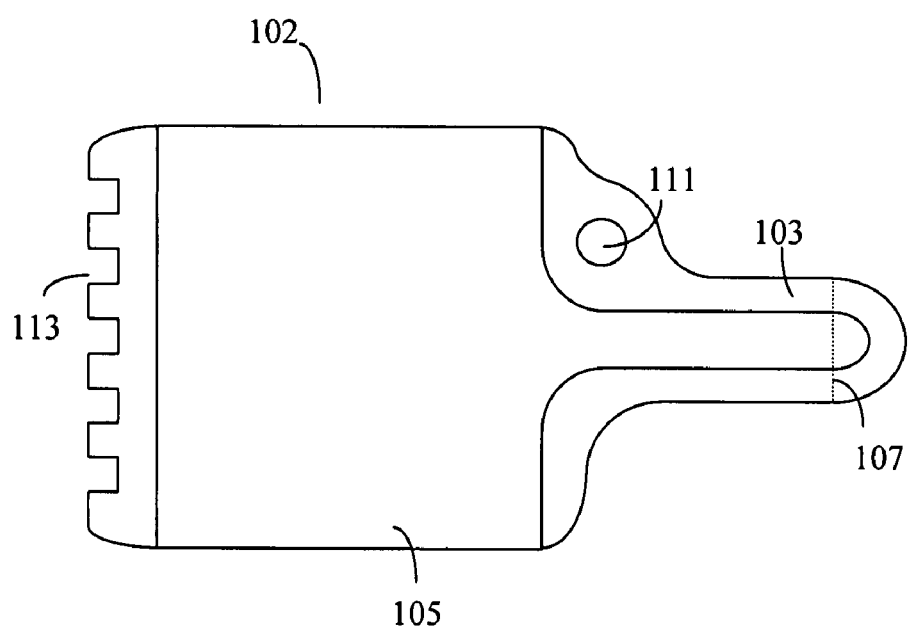
FIG. 2 illustrates a second embodiment of the packet containing the gel medication.

In an embodiment, the packets 101 are formed from a clear plastic material. The fabrication process can include the steps of heating a portion of the plastic tube stock with a heated die that fuses the sheet stock together to form the elongated section of the packet. The fused sections are represented in FIGS. 1 and 2 as the outer areas around the body section 105 and nozzle section 103. The tube stock is then cut and the packet is filled with the gel medication. The open end is then fused to seal the gel medication within the packet 101, 102. The end of the packet can be formed into a straight edge 109 or pattered edge 113 that can be used to spread the gel medication across the hoof. In a preferred embodiment, a machine draws the plastic tube stock from a source such as a roll and then seals, cuts and fills the packet with the gel medication as described above.

In some embodiments, the packet 101, 102 can be imprinted words onto the packet such as contents, instructions, warnings, product names, brand name, etc. The printing can be through an ink printing or through etching of the plastic packet material. The machine may also form a hole 111 that allows the packet 101, 102 to be secured to a rod, hook or loop. The plastic stock is preferably clear so that the user can see the blue copper sulfate gel within the packet 101, 102 and determine if the entire contents have been removed before disposing of the packet 101, 102. The packet 101, 102 may also have serrations 107 or other markings indicating where to cut the nozzle section 103 to open the packet 101, 102. While the packet 101, 102 is described as being fabricated from a tube stock, in other embodiments the packets are formed from two or more elongated sheets of plastic that are fused together to form the body section 105 and nozzle section 103 of the packet 101, 102. In still other embodiments, the packet 101, 102 is molded from liquid plastic or any other plastic fabrication method.

As discussed, once the gel medication is applied to the frog and sole of the hoof, it should be spread across these surfaces so that all of the fungus can be treated. This spreading can be done with a user's gloved hands, however this task can also be performed with the edge 109 portion of the packet 101 itself. In an embodiment, a portion of the packet 101 includes a flexible straight edge 109 that can have rounded corners. This straight edge 109 can be used to evenly spread the gel across the frog and sole.

In another embodiment of the packet 102 with reference to FIG. 2, a grooved edge 113 can be used to spread the gel. The grooves 115 in the straight edge provide a more flexible surface that can more easily adjust to the contours of the frog and sole. The thickness of the plastic and the depth of the grooves 115 controls the stiffness of the edge. A thin plastic having deep grooves 115 will be very flexible, while a thicker plastic having shallow or no grooves 115 will be stiffer. It is contemplated that various other edge designs can be formed which will be able to spread the gel medication across the hoof.

The surface area of a frog and sole may range from about 40 to 74 square inches. In a preferred embodiment, the packet may contain a single dosage of about 0.5 ounce, which will provide a layer of gel medication that is about 0.045 to 0.024 inch thick across the hoof. The single dose packet allows the user to open the packet, disperse the treatment contents onto one horse hoof and then dispose of the packet. Since the entire packet contents are used, there is no need to remove single dosages from bulk volumes of the medication stored in large containers. Thus, the single dose packet also reduces the chances of contact with the copper sulfate. Although the active ingredient in the gel medication has been described as copper sulfate, various other medications can be used. Other suitable fungicides that can be mixed into the gel include: zinc sulfate, iron sulfate, and magnesium sulfate, zinc oxide, magnesium oxide, bleach, and other fungicides.

A horse shoe is typically attached to the hoof which protects the outer perimeter but leaves the sole and frog exposed. This exposure can result in the medication being washed away as the horse walks across the ground. The growth or dirt that can contact the sole and frog can remove the medicated gel.

Figure 3:
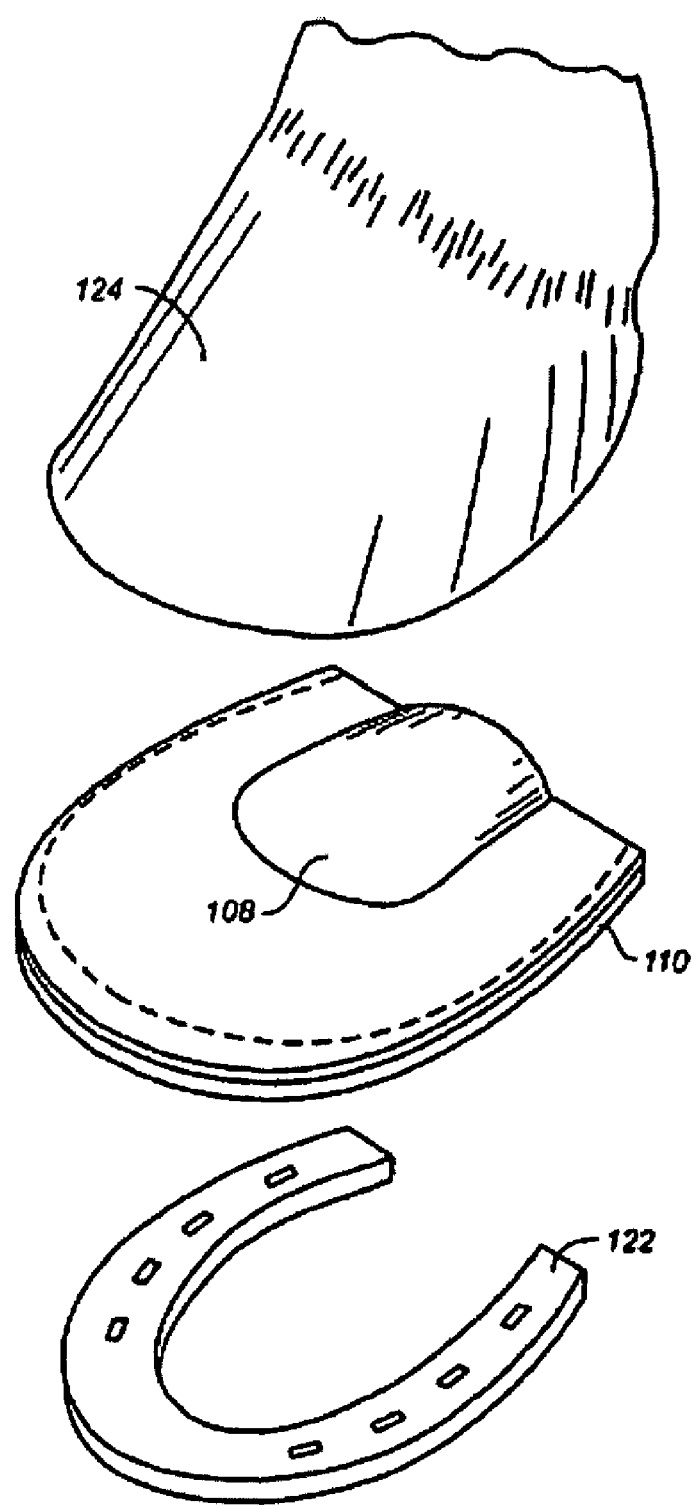
FIG. 3 illustrates a horse hoof, support pad and horseshoe.
Figure 4:
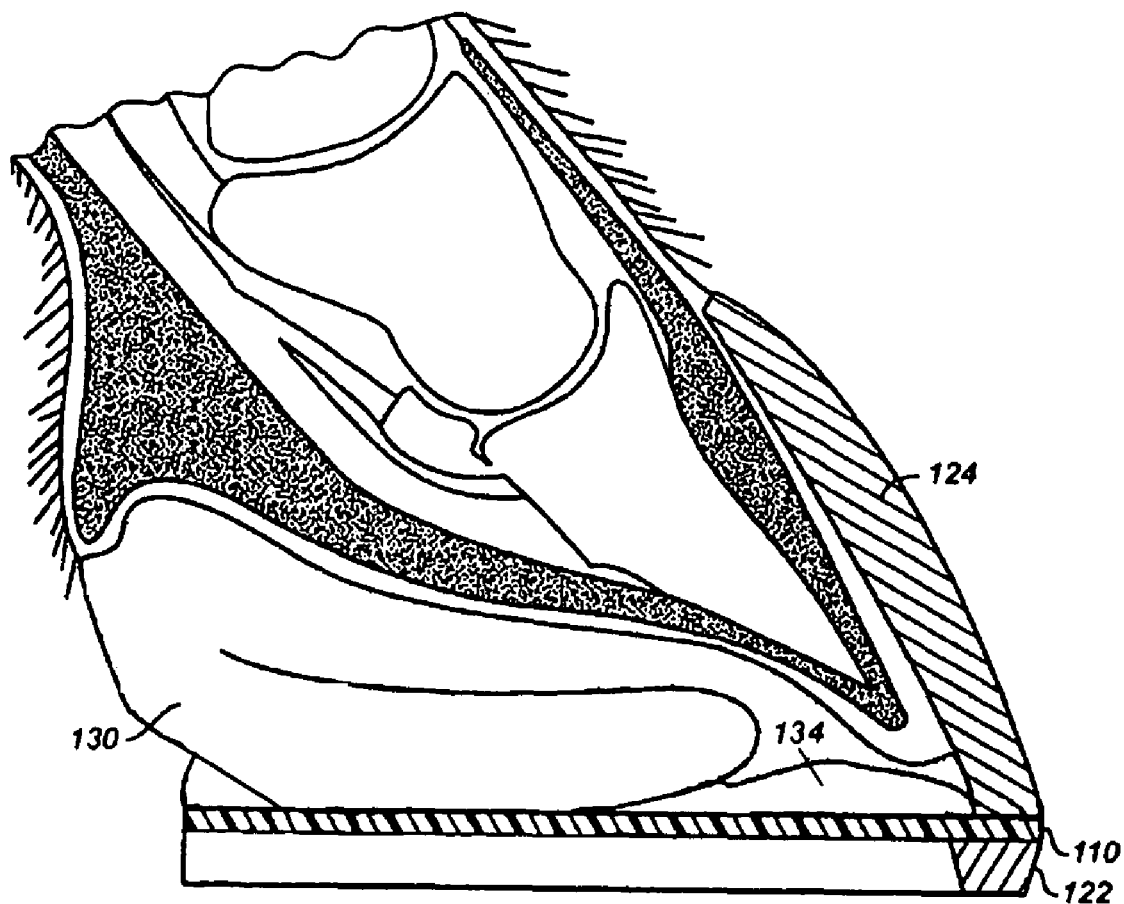
FIG. 4 illustrates a cross section of the horse hoof, support pad and horseshoe.

With reference to FIGS. 3 and 4, in an embodiment a support pad 110 can be placed across the hoof 124 to cover the sole 134 and frog 130. In an embodiment, the support pad 110 can be held in place between the shoe 122 that is typically nailed to the hoof 124. In an embodiment, the support pad 110 includes a lower piece made of a rigid plastic and/or hard rubber material that is roughly the shape of the horseshoe 122. In an embodiment, the support pad 110 also includes an inflatable bladder made of a softer material that is mounted to the upper surface towards the rear center of the support pad 110. The inflatable bladder can be coupled to a valve which allows the bladder 108 to be pressurized with a compressible fluid such as air or nitrogen.

In one embodiment, the gel medication can be applied to the hoof 124 before the support pad 110 is attached to the hoof 124. In another embodiment, the gel is applied after the support pad 110 is attached. The nozzle end of the gel pack can be opened and inserted into the opening of the horseshoe 122 at the back of the hoof 124. The gel pack can then be squeezed to apply the gel to the frog 130 and sole 134. Since the frog 130 and sole 134 are covered by the pad 110, it can be difficult to spread the gel. Because the support pad is flexible, it can be physically pressed against the frog 130 and sole 134 to spread the gel around the frog 130 and sole 134. If the support pad 110 includes an inflatable bladder, the bladder can be deflated prior to applying the gel and re-inflated after the gel is applied to the frog 130 and sole 134. The compression of the upper surface of the bladder 108 against the hoof 124 can cause the gel to be spread across the frog 130 and sole 134.

In an embodiment, the support pad 110 can be made of a transparent or translucent elastic material. In this embodiment, the user can see through the support pad 110 in the area surrounded by the shoe 122 to determine if the gel is still properly spread across the hoof 124. In this embodiment, it can be particularly useful to use a gel that has a contrasting appearance to the hoof 124. If the gel having a contrasting color cannot be seen, the user will be informed that a new dosage of the gel may be required.

It will be understood that although the present invention has been described with reference to particular embodiments, additions, deletions and changes could be made to these embodiments, without departing from the scope of the present invention. Although a method has been described that includes components and process steps, it is well understood that these components and methods can be modified and rearranged in various other configurations and processes.

What is claimed is:

1. A method for treating an infection of a hoof comprising:
mixing a gel containing 5-30% water, 40-80% glycerin and 5-30% copper sulfate;
inserting the gel into a flexible packet having a body section and an elongated section;
sealing the packet;
cutting the elongated section of the packet to open the packet;
compressing the body section so that the gel is ejected from the packet to the hoof;
applying the gel to the hoof;
heating the gel so that the viscosity of the gel is lowered, causing the gel to spread to recessed surfaces of the hoof; and
controlling the growth of the infection by exposing infected areas of the hoof to the copper sulfate.

2. The method of claim 1 further comprising:
forming a substantially straight edge on the packet;
spreading the gel across the hoof using the straight edge.

3. The method of claim 1 further comprising:
forming a jagged edge on the packet;
spreading the gel across the hoof using the jagged edge.

4. The method of claim 1 further comprising:
protecting an area of the hoof covered with the gel.

5. The method of claim 1 further comprising:
attaching a substantially planar elastic member across the hoof to protect the hoof.

6. The method of claim 5 further comprising:
attaching the substantially planar elastic member between the hoof and a shoe to protect the hoof.

7. The method of claim 1 wherein the viscosity of the gel at ambient temperature is approximately 5 to 60 cP.

8. The method of claim 1 wherein the volume of the packet is approximately 0.25-1.50 oz.

9. A method for treating thrush of a hoof comprising:
providing a sealed packet having a body section and an elongated section containing a gel that is a mixture of 5-30% water, 40-80% glycerin and 5-30% copper sulfate;
opening the packet at the elongated section;
directing the elongated section towards the hoof;
compressing the body section so that the gel is ejected;
applying the gel to areas of the hoof that are infected;
heating the gel so that the viscosity of the gel is lowered, causing the gel to spread to recessed surfaces of the hoof; and
controlling the growth of the infection by exposing the areas of the hoof that are infected to the copper sulfate.

10. The method for treating thrush of claim 9, further comprising:
running an animal so the hoof contacts the ground; wherein the impact of the hoof causes the gel to heat so that the viscosity of the gel is lowered and the gel is spread to recessed surfaces of the hoof.

11. The method for treating thrush of claim 9, further comprising:
spreading the gel on the hoof with a portion of the packet.

12. The method of claim 9 further comprising:
attaching a substantially planar elastic member across the hoof to protect the hoof.

13. The method of claim 9 further comprising:
attaching the substantially planar elastic member between the hoof and a shoe to protect the hoof.

14. A method for treating an infection of a hoof comprising:
providing a sealed packet containing a gel that is a mixture of 5-30% water, 40-80% glycerin and 5-30% copper sulfate or zinc sulfate that has a viscosity of about 15 to 40 cP;
opening the packet;
compressing the packet so that the gel is ejected;
applying the gel to areas of the hoof that are infected;
heating the gel so the viscosity is reduced to less than 10 cP;
absorbing the gel into the hoof; and
controlling the growth of the infection by exposing the areas of the hoof that are infected to the copper sulfate or zinc sulfate.

15. The method for treating thrush of claim 14, further comprising:
running an animal so the hoof contacts the ground; wherein the impact of the hoof causes the gel to heat so that the viscosity of the gel is lowered and the gel is spread to recessed surfaces of the hoof.

16. The method for treating thrush of claim 14, further comprising:
spreading the gel to recessed surfaces of the hoof with a portion of the packet.

17. The method of claim 14 further comprising:
attaching a substantially planar elastic member across the hoof to protect the hoof.

18. The method of claim 17 further comprising:
attaching the substantially planar elastic member between the hoof and a shoe to protect the hoof.

* * * * *